(12) United States Patent
Hoffmann et al.

(10) Patent No.: US 11,186,869 B2
(45) Date of Patent: Nov. 30, 2021

(54) SEQUENCING DEVICE AND METHOD FOR OPERATING A SEQUENCING DEVICE

(71) Applicant: Robert Bosch GmbH, Stuttgart (DE)

(72) Inventors: Jochen Hoffmann, Renningen (DE); Karin Lemuth, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 76 days.

(21) Appl. No.: 16/190,308

(22) Filed: Nov. 14, 2018

(65) Prior Publication Data

US 2019/0106743 A1  Apr. 11, 2019

Related U.S. Application Data

(62) Division of application No. 15/074,448, filed on Mar. 18, 2016, now Pat. No. 10,160,999.

(30) Foreign Application Priority Data

Mar. 25, 2015 (DE) ..................... 10 2015 205 435.7

(51) Int. Cl.
| | |
|---|---|
| *C12Q 1/6869* | (2018.01) |
| *C12N 1/06* | (2006.01) |
| *G01N 33/487* | (2006.01) |
| *B01L 3/00* | (2006.01) |

(52) U.S. Cl.
CPC ............ *C12Q 1/6869* (2013.01); *B01L 3/502* (2013.01); *C12N 1/06* (2013.01); *G01N 33/48721* (2013.01); *B01L 2200/10* (2013.01); *B01L 2300/0636* (2013.01); *B01L 2300/0864* (2013.01); *B01L 2400/0421* (2013.01)

(58) Field of Classification Search
CPC .... C12Q 1/6869; G01N 33/4871; B01L 3/502
See application file for complete search history.

(56) References Cited

U.S. PATENT DOCUMENTS

| | | | |
|---|---|---|---|
| 7,468,271 B2 | 12/2008 | Golovchenko | |
| 8,372,629 B2 | 2/2013 | Southern | |
| 10,030,240 B2 * | 7/2018 | Shirai | ........................ B01L 7/52 |
| 2004/0001371 A1 * | 1/2004 | Mansuripur | ....... G11C 13/0019 365/200 |
| 2006/0240543 A1 | 10/2006 | Folch et al. | |

(Continued)

FOREIGN PATENT DOCUMENTS

| | | |
|---|---|---|
| DE | 10 2012 216 497 A1 | 3/2014 |
| DE | 10 2013 217 694 A1 | 3/2015 |

(Continued)

OTHER PUBLICATIONS

Gillooly et al, Nuclear DNA Content Varies with Cell Size across Human Cell Types, 2015, Cold Spring Harb Perspect Biol., 7, a019091, pp. 1-27 (Year: 2015).*

(Continued)

*Primary Examiner* — Narayan K Bhat
(74) *Attorney, Agent, or Firm* — Maginoit, Moore & Beck LLP

(57) ABSTRACT

A sequencing device has at least one sequencing channel configured to fluidically connect a first gap with a second gap. The sequencing channel is formed as a cavity in the region of the first gap and is formed as a pore in the region of the second gap. The pore has a smaller cross section than the cavity.

18 Claims, 3 Drawing Sheets

(56) References Cited

U.S. PATENT DOCUMENTS

| | | |
|---|---|---|
| 2008/0213872 A1 | 9/2008 | Regan |
| 2010/0292101 A1 | 11/2010 | So |
| 2011/0005932 A1* | 1/2011 | Jovanovich .............. G01N 1/31 204/453 |
| 2011/0168562 A1* | 7/2011 | Nuckolls .............. C12Q 1/6869 204/600 |
| 2014/0349867 A1* | 11/2014 | Handique ............ C12Q 1/6844 506/9 |
| 2016/0010078 A1 | 1/2016 | Shirai |

FOREIGN PATENT DOCUMENTS

| | | |
|---|---|---|
| GB | WO 2016/117541 | * 11/2016 |
| WO | 2010/117470 A2 | 10/2010 |
| WO | 2013/191793 A1 | 12/2013 |
| WO | 2014/141386 A1 | 9/2014 |
| WO | 2014/151250 A1 | 9/2014 |

OTHER PUBLICATIONS

Schultz et al, Big Bacteria, 2001, Annu. Rev. Microbiol., 55, 105-137. (Year: 2001).*

* cited by examiner

SEQUENCING DEVICE AND METHOD FOR OPERATING A SEQUENCING DEVICE

This application is a divisional application of U.S. application Ser. No. 15/074,448, filed on Mar. 18, 2016, which claims priority under 35 U.S.C. § 119 to patent application number DE 10 2015 205 435.7, filed on Mar. 25, 2015 in Germany, the disclosures of which are incorporated herein by reference in their entirety.

BACKGROUND

The disclosure proceeds from a sequencing device or a method according to the following description. The subject matter of the present disclosure is also a computer program.

The decoding of the genetic code is also referred to as DNA sequencing and is frequently used in science, medicine and forensics. Up to now, a comprehensive sample preparation, such as lysis and purification, is indispensable for the purposes of sequencing, in order to obtain sufficiently pure nucleic acids for sequencing.

SUMMARY

Against this background, the approach introduced here presents a sequencing device and additionally a method for operating a sequencing device, a device for controlling such a method and lastly a corresponding computer program according to the following description. Advantageous developments and improvements of the device specified in the following description are possible by means of the measures listed in the following description.

There is presented a sequencing device having at least one sequencing channel which fluidically connects a first gap with a second gap, wherein the sequencing channel is formed as a cavity in the region of the first gap and is formed as a pore in the region of the second gap, wherein the pore has a smaller cross section than the cavity.

A sequencing device can be understood to mean a device for determining a DNA sequence. The DNA sequence can be evaluated by a conventional evaluation unit. A gap can be a channel for guiding one medium or for guiding a plurality of media. In particular, the first gap can be formed by a clearance between a base body of the device and a first planar substrate. The second gap can be formed by a clearance between the base body and a second planar substrate. In this connection, the substrates can be arranged on opposite sides of the base body. The substrates can be arranged substantially parallel to one another. A sequencing channel can break through or open the base body. A cavity can be referred to as a (broad) indentation in a base body having a fluidic passage into the (narrow) pore, the pore likewise forming an opening of the base body. The cavity can also be referred to as a well. The cross section of the pore is (substantially) smaller than the cross section of the cavity, for example smaller than the cross section of the cavity by one order of magnitude. A cross section can be understood here to mean a cross-sectional area or a clearance between two opposite edges of the cavity and/or of the pore in the region of the formation of the cross section. The cross section can also form a diameter of the sequencing channel when the sequencing channel has a circular base area. At the same time, the pore can have a length which substantially corresponds to a depth of the cavity.

The exemplary single-molecule sequencer presented here omits a clonal amplification of the DNA molecules or nucleic acids to be sequenced, and, as a result, there is no sequencing bias. Similarly, bridge amplification is not required. In addition, a complicated sample preparation can be dispensed with.

A microfluidic environment is presented, which environment makes it possible to individually disrupt cells in a sample solution, to purify the DNA and to individually sequence said DNA directly afterwards in downstream pores.

The system presented here allows a genuine single-cell sequencing process. As a result, it is possible, using a plurality of sequencing channels, to determine the genetic heterogeneity of a sample solution containing cells.

There is a high sensitivity of the entire system, since purification, for example by means of a column, involving high losses during purification in the case of small DNA concentrations is omitted.

The system presented here further allows the analysis of very small cell amounts, since each cell can be separately disrupted in one well of the microwell array and sent for nanopore sequencing.

There is no longer a need for a separate sample purification for a sequencing process; all the individual steps or individual methods can be represented and carried out in a single microfluidic environment. This lowers the error rate of the entire system and the time invested.

The system presented here rules out a DNA contamination of the DNA or cells to be sequenced, since the cell lysates are fed into the actual sequencing process in an automated and integrated manner, avoiding DNA carryover and contamination, which could adversely affect the sequencing result.

To this end, the cavity can be designed to accommodate an individual cell. To this end, the cavity can be small enough to allow precisely one individual cell to fit in. More particularly, the cavity can have a cross section between one micrometer and three hundred micrometers. More particularly, the cavity can have a cross section between three micrometers and 30 micrometers.

The first gap and, alternatively or additionally, the second gap can have a gap width between two micrometers and one millimeter. More particularly, the first gap and, alternatively or additionally, the second gap can have a gap width between five micrometers and 500 micrometers. The gap width can be adjusted depending on the media used for the purposes of sequencing preparation and for the purposes of sequencing itself. More particularly, the gap width can be optimized for a laminar flow within the gaps.

An electrophoresis path can be arranged in the pore. This makes it possible to directly use the sequencing device presented here for an electrophoresis process.

The sequencing device can have at least one further sequencing channel. More particularly, a multiplicity of sequencing channels can be arranged to form a matrix. More particularly, the matrix can have a density between $1 \times 10^3$ and $25 \times 10^6$ sequencing channels per square centimeter. By means of many sequencing channels, it is possible to carry out many sequencing processes at the same time.

Furthermore, there is presented a method for operating a microfluidic sequencing device having at least one microfluidic sequencing channel which fluidically connects a first microfluidic gap with a second microfluidic gap, wherein the sequencing channel is formed as a cavity in the region of the first gap and is formed as a pore in the region of the second gap, wherein the pore has a smaller cross section than the cavity, wherein the method comprises the following steps: feeding a sample solution into the first gap in order to introduce a cell into the cavity;

lysing the cell into its cellular constituents in order to release cellular DNA of the cell;

rinsing the first gap in order to remove undesired cellular constituents of the cell from the cavity and/or the first gap and to isolate the DNA in the cavity;

filling the first gap and the second gap with a sequencing buffer; and sequencing the DNA in the pore.

An aqueous solution containing cells can be fed in as sample solution.

In the feeding step, a centrifugation, a sedimentation and, alternatively or additionally, a vacuum treatment can be further carried out in order to introduce the cell into the cavity. As a result, it is possible to sequence the individual cells at specific sites and to speed up the sequencing process.

In the lysis step, a chemical lysis, an enzymatic lysis, an electrical lysis, an ultrasonic lysis and, alternatively or additionally, a thermal lysis can, for example, be carried out in order to release the cellular DNA. In the sequencing device presented here, it is possible to carry out and/or combine different lysis methods.

This means that different cells can be lysed.

In the lysis step, an organic phase (i.e. liquid) can be introduced into the first gap. More particularly, the organic phase can be introduced into the first gap by means of a laminar flow. The organic phase can have a low solubility in the aqueous solution. Because of the laminar flow, it is possible to avoid turbulences.

In the rinsing step, a rinse liquid can be introduced into the first gap. More particularly, the rinse liquid can be introduced into the first gap by means of a laminar flow. The rinse liquid can easily remove or displace a lysis liquid. The rinse liquid can itself be easily removed from the gap. Because of the laminar flow, it is possible to avoid turbulences.

In the sequencing step, an electric voltage can be applied between a first substrate bounding the first gap and a second substrate bounding the second gap in order to sequence the DNA in the pore. Because of a resultant electric field, it is possible to sequence the DNA by means of electrophoresis.

This method can, for example, be implemented in software or hardware or in a mixed form composed of software and hardware, for example in a control unit.

The approach presented here further provides a device designed to carry out, control or realize the steps of a variant of a method presented here in corresponding units. This embodiment variant of the disclosure in the form of a device can also rapidly and efficiently achieve the object underlying the disclosure.

A device can be understood here to mean an electrical instrument which processes sensor signals and outputs control and/or data signals depending on said sensor signals. The device can have an interface which can be hardware-based and/or software-based. In the case of a hardware-based design, the interfaces can, for example, be part of a so-called system ASIC, which includes a very wide variety of different functions of the device. However, it is also possible for the interfaces to be distinct, integrated circuits or to at least partly consist of discrete components. In the case of a software-based design, the interfaces can be software modules which are, for example, present on a microcontroller in addition to other software modules.

Also of advantage is a computer program product or computer program containing program code which can be stored on a machine-readable carrier or storage medium such as a semiconductor memory, a hard disk storage medium or an optical storage medium and is used to carry out, realize and/or control the steps of the method according to any of the above-described embodiments, especially when the program product or program is executed on a computer or a device.

BRIEF DESCRIPTION OF THE DRAWINGS

Exemplary embodiments of the disclosure are depicted in the drawings and elucidated in detail in the following description.

In the following description of favorable exemplary embodiments of the present disclosure, identical or similar reference signs are used for the elements which are shown in the various figures and act in a similar manner, with a repeated description of said elements being dispensed with.

DETAILED DESCRIPTION

Figure 1:
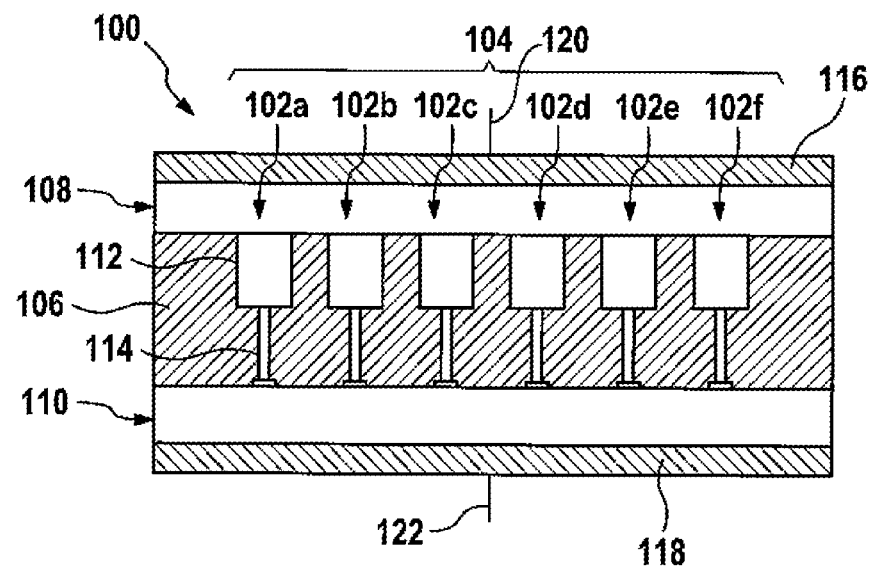
FIG. 1 shows a diagram of a sequencing device according to one exemplary embodiment.

FIG. 1 shows a diagram of a sequencing device 100 according to one exemplary embodiment. The sequencing device 100 has a plurality of sequencing channels 102. The diagrammatic plane selected here shows a first sequencing channel 102a, a second sequencing channel 102b, a third sequencing channel 102c, a fourth sequencing channel 102d, a fifth sequencing channel 102e and a sixth sequencing channel 102f next to one another. The sequencing channels 102 are similar. The sequencing channels 102 are arranged to form a matrix 104. The sequencing channels 102 are formed in a plate-shaped base body 106. Each of the sequencing channels 102 represents a fluidic connection between a first gap 108 on a first side of the base body 106 and a second gap 110 on an opposing second side of the base body 106.

The sequencing channel 102 is formed as a cavity 112 in the region of the first gap 108. In the region of the second gap 110, the sequencing channel 102 is formed as a pore 114. In this connection, the pore 114 has a (substantially) smaller cross section than the cavity 112. More particularly, the cavity 112 is designed to accommodate an individual cell to be sequenced. For example, the cross section or diameter of the cavity is 100- to 100 000-fold larger than the cross section or diameter of the pore.

In the exemplary embodiment shown, the first gap 108 is formed between the base body 106 and a lid substrate 116 and has a gap width designed to allow a laminar flow in the first gap 108.

The second gap 110 is formed here between the base body 106 and a bottom substrate 118. The second gap 110 likewise has a gap width designed to allow a laminar or nonlaminar flow in the second gap 108.

The lid substrate 116 has a first electrical connection 120 for electrical contacting of the lid substrate 116.

The bottom substrate 118 has a second electrical connection 122 for electrical contacting of the bottom substrate 118.

An electric voltage can be applied between the two electrical contacts 120, 122 in order to generate an electric field between the lid substrate 116 and the bottom substrate 118.

A cross section through a microwell nanopore hybrid 100 is shown. The microwell array 104 has cavities 112 opened toward the surface of the microwell array 104. The cavities 112 can be referred to as wells 112. Connected to the underside of the wells 112 is a pore 114 or nanopore 114 in each case.

Between the microwell surface and a lid substrate 116, there is a microfluidic gap 108 with dimensions of two to 1000 μm, preferably five to 500 μm. Between the underside of the microwell array 104 and the bottom substrate 118, there is likewise a microfluidic gap 110 with dimensions of two to 1000 μm, preferably five to 500 μm. The clearance is selected such that a laminar through-flow is promoted. An electric field can be applied between the lid substrate 116 and the bottom substrate 118.

In the microwell array 104 presented here, the dimensions of a well 112 can be between 500 nm and 300 μm, preferably between one μm and 30 μm. The density of the wells 112 on the microwell array 104 can be between $1 \times 10^3$ and $25 \times 10^6$ wells 112 per $cm^2$.

The approach presented here can be used for analytical systems, especially for microfluidic lab-on-a-chip systems for environmental analysis or medical diagnostics.

Figure 2:
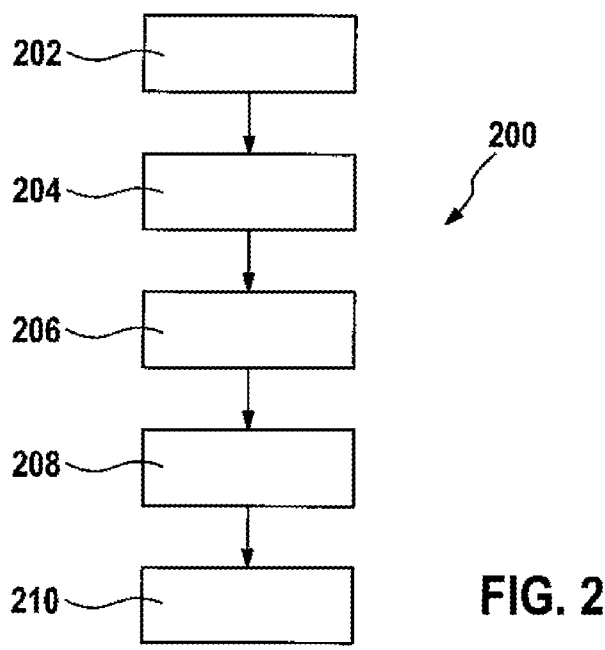
FIG. 2 shows a flowchart of a method for operating a sequencing device according to one exemplary embodiment.

FIG. 2 shows a flowchart of a method 200 for operating a sequencing device according to one exemplary embodiment. The method 200 can be carried out on a sequencing device, as shown in FIG. 1. To this end, the sequencing device is connected to a device for operating the sequencing device. More particularly, the sequencing device is designed as a single-use cartridge which is connected via interfaces to the operating device.

The method 200 has a feeding step 202, a lysis step 204, a rinsing step 206, a filling step 208 and a sequencing step 210. In the feeding step 202, a sample solution is fed into the first gap in order to introduce an individual cell into at least one of the cavities. For example, for the purposes of feeding, a negative pressure is established in the first gap in order to suck the sample solution into the first gap and thus into the cavities. Similarly, the sample solution can be pressed into the first gap by means of a positive pressure. Alternatively, the sample solution can be drawn into the gap as a result of the capillary effect. In the lysis step 204, the at least one cell is broken up within its cavity into its cellular constituents in order to release cellular DNA of the cell. The lysis can be achieved in different ways. For example, in the lysis step 204, a chemical lysis, an enzymatic lysis, an electrical lysis, an ultrasonic lysis and, alternatively or additionally, a thermal lysis can be carried out in order to release the cellular DNA. In the rinsing step 206, the first gap is rinsed in order to remove undesired cellular constituents of the cell from the cavity and, alternatively or additionally, from the first gap and to isolate the DNA in the cavity. More particularly, a rinse fluid can be guided through the first gap, which fluid selectively removes all cellular constituents apart from the DNA from the cavity. In the filling step 208, the first gap and the second gap are filled with a sequencing buffer. As in the feeding step 202, the sequencing buffer can be sucked or drawn and/or pressed into the gap. In the sequencing step 210, the DNA is sequenced in the pore.

In step 202, a centrifugation, a sedimentation and, alternatively or additionally, a vacuum treatment can be further carried out in order to introduce the cell into the cavity.

Figure 3:
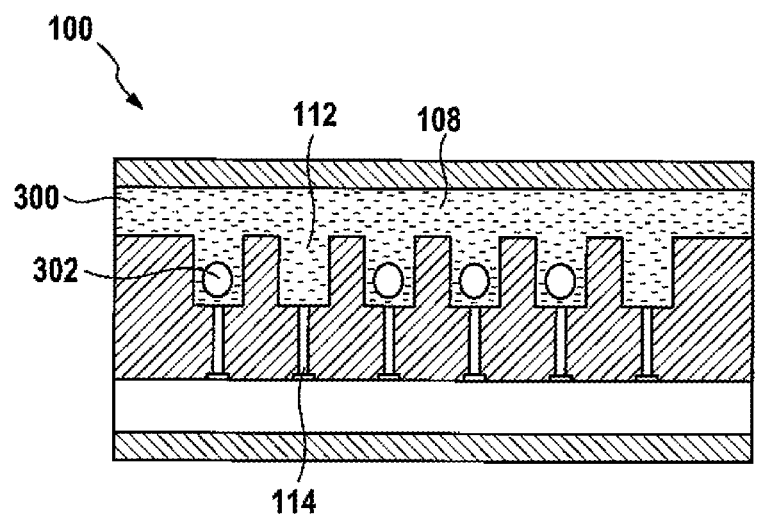
FIG. 3 shows a diagram of feeding of a sample solution into a sequencing device according to one exemplary embodiment.

FIG. 3 shows a diagram of feeding of a sample solution 300 into a sequencing device 100 according to one exemplary embodiment. In this case, the sequencing device 100 substantially corresponds to the sequencing device in FIG. 1. Feeding represents one step of a method for operating the sequencing device, as described in FIG. 2.

Here, an aqueous solution 300 containing cells 302 is fed into the first gap 108. While this is done, the cavities 112 are likewise wetted with the aqueous solution 300. The cells 302 are introduced into the cavities 112 by means of a centrifugation, a sedimentation and, alternatively or additionally, a vacuum treatment. During this action, only one cell 302 fits into each cavity 112. As a result, the individual cells 302 are isolated from one another.

What is shown is an exemplary embodiment for a purification of the cellular DNA. In this case, a miniaturized phenol/chloroform extraction is used. To this end, the cells 302 to be analyzed in water or a sample solution 300 containing cells 302 are introduced into the chip 100.

Figure 4:
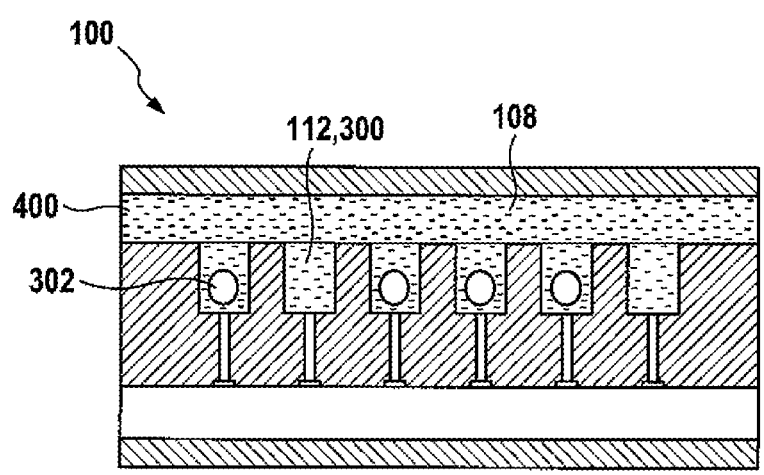
FIG. 4 shows a diagram of lysis of cells in a sequencing device according to one exemplary embodiment.

FIG. 4 shows a diagram of lysis of cells 302 in a sequencing device 100 according to one exemplary embodiment. In this case, the sequencing device 100 substantially corresponds to the sequencing device in FIG. 1. Lysis represents one step of a method for operating the sequencing device, as described in FIG. 2.

In said step, the first gap 108 is filled with a lysis liquid 400. The lysis liquid 400 brings about a lysis of the cells 302, involving the cells being broken up into their cellular constituents. Alternatively, the cells can be electrically lysed by application of an electric field between 120 and 122. The lysis liquid 400 for example penetrates the cavities 112 only insignificantly because of its surface tension. A remainder of the aqueous solution 300 remains in each of the cavities 112.

Following the introduction, the microfluidic gap 108 is filled with an organic phase 400, in this case phenol in a 1:1 ratio. The DNA, cellular fragments and cellular contents present in the aqueous solution 300 are separated owing to their different solubilities. The DNA remains in the aqueous phase 300; all the other constituents pass over into the organic phase 400 by diffusion. Said constituents are removed from the chip 100 by subsequent rinsing out of the organic phase 400, for example using chloroform and isoamyl alcohol, for example in a 24:1 ratio.

In other words, FIGS. 3 and 4 show figures in the form of intermediate stages in a sample preparation procedure for a nanopore sequencing process according to the approach presented here.

For the purposes of sample preparation, a sample solution containing cells is fed into the microfluidic gap in FIG. 3. The cells are introduced into the wells by means of centrifugation, sedimentation or with the aid of vacuum. Thereafter, the cells are lysed in FIG. 4. To this end, known methods can be used, such as a chemical lysis, an enzymatic lysis, an electrical lysis, an ultrasonic lysis and/or a thermal lysis.

Figure 5:
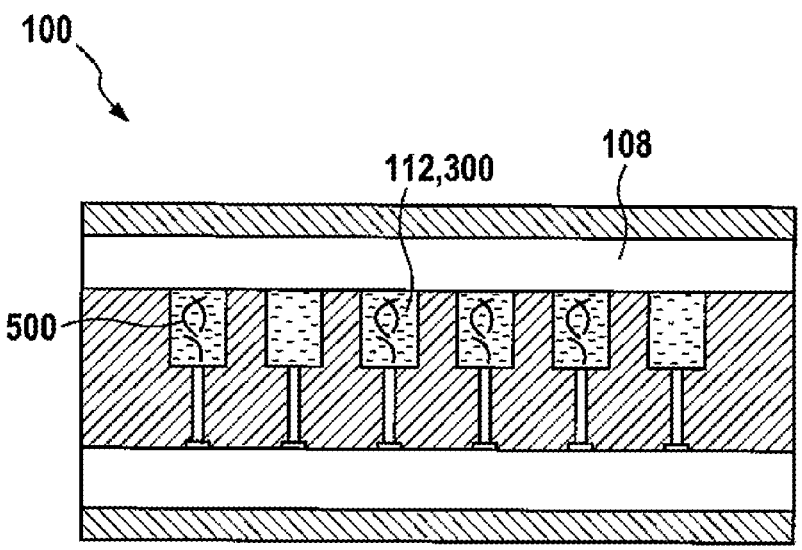
FIG. 5 shows a diagram of isolated DNA in a sequencing device according to one exemplary embodiment.

FIG. 5 shows a diagram of isolated DNA 500 in a sequencing device 100 according to one exemplary embodiment. In this case, the sequencing device 100 substantially corresponds to the sequencing device in FIG. 1. Here, the lysis liquid or a rinse liquid subsequently introduced into the first gap 108, from FIG. 4, has been removed from the first gap 108. The remainder of the aqueous solution 300 containing the DNA 500 is arranged in each cavity 112.

What is shown is the chip 100 after purification. Here, cellular DNA 500 is present isolated in an aqueous phase 300 in the various wells 112.

Figure 6:
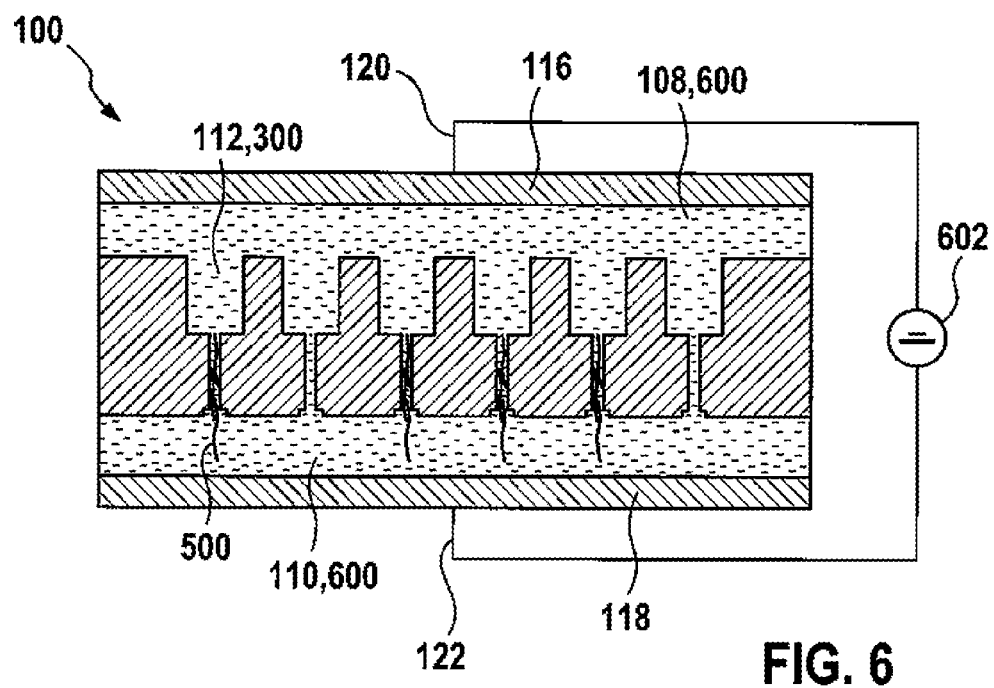
FIG. 6 shows a diagram of sequencing of DNA in a sequencing device according to one exemplary embodiment.

FIG. 6 shows a diagram of sequencing of DNA 500 in a sequencing device 100 according to one exemplary embodiment. In this case, the sequencing device 100 substantially corresponds to the sequencing device in FIG. 1. Sequencing represents one step of a method for operating the sequencing device, as described in FIG. 2.

Here, a sequencing medium 600 is introduced into the first gap 108 and the second gap 110. The pores 114 are likewise filled with the sequencing medium 600. At the same time, the aqueous solution 300 is initially arranged in the cavities 112. The aqueous solution mixes with the sequencing medium by means of diffusion. As a result, the cavities are filled with the sequencing medium (the aqueous solution is diluted out). A DC voltage source 602 is activated between the electrical connections 120, 122. This forms an electric field between the lid substrate 116 and the bottom substrate 118. The electric field pulls the DNA through the pores 114, and a migration rate of the DNA 500 or fragments of the DNA 500 in the sequencing medium 600 can be evaluated.

What is shown is an exemplary embodiment of a sequencing process. To this end, the microfluidic gaps 108, 110 are filled with a sequencing buffer 600. The pores 114 have an electrophoresis path, for example the same buffer 600 with which the gaps 108, 110 are also filled or an agarose gel.

When a voltage is applied to the lid substrate 116 and the bottom substrate 118, the cellular DNA 500 of each well 112 is conducted through the pores 114 connected to the wells 112.

The detection of the fragment length of the DNA 500 and/or the detection of specific bases can be achieved using known methods. For example, the detection can be achieved by electrical, electrochemical or optical means. Different buffers 600 can be used depending on the detection method. For example, it is possible to use 1 M KCl salt solution containing 10 mM Tris-HCl and 1 mM EDTA (ethylenediaminetetraacetic acid), pH 8.0 at room temperature or 3 M KCl solution, pH 10.4, containing 1 mM EDTA for the electrical detection using a solid-state nanopore.

If an exemplary embodiment comprises an "and/or" link between a first feature and a second feature, this is to be read as meaning that the exemplary embodiment has, according to one embodiment, both the first feature and the second feature and, according to a further embodiment, either only the first feature or only the second feature.

What is claimed is:

1. A sequencing device, comprising:
   a microfluidic sequencing channel configured to fluidically connect a first microfluidic gap with a second microfluidic gap;
   a memory including program instructions; and
   a processor operably connected to the memory, wherein the microfluidic sequencing channel is formed as a cavity in a region of the first microfluidic gap and is formed as a pore in a region of the second microfluidic gap,
   the cavity is sized to fit only one cell, of a plurality of cells within a sample solution, completely therein,
   the cavity is configured to accommodate a lysis fluid in addition to the only one cell of the plurality of cells,
   the cavity has a cross section between five hundred nanometers and three hundred micrometers,
   the pore has a cross section which is smaller than a cross section of the cavity,
   the pore is configured to sequence cellular DNA in the pore, and
   the processor is configured to execute the program instructions to
   feed the sample solution into the first microfluidic gap in order to introduce the only one cell into the cavity,
   lyse the only one cell into its cellular constituents in order to release cellular DNA of the cell, and
   sequence the cellular DNA in the pore.

2. The sequencing device according to claim 1 wherein the cavity has a cross section between one micrometer and thirty micrometers.

3. The sequencing device according to claim 1, wherein at least one of the first microfluidic gap and the second microfluidic gap has a gap width between two micrometers and two millimeters.

4. The sequencing device according to claim 3, wherein the at least one of the first microfluidic gap and the second microfluidic gap has a gap width between five micrometers and 500 micrometers.

5. The sequencing device according to claim 1, wherein an electrophoresis path is provided in the pore.

6. The sequencing device according to claim 1, further comprising at least one further microfluidic sequencing channel.

7. The sequencing device according to claim 6, wherein the at least one further microfluidic sequencing channel includes a multiplicity of sequencing channels arranged to form a matrix.

8. The sequencing device according to claim 7, wherein the matrix has a density between $1 \times 10^3$ and $25 \times 10^6$ microfluidic sequencing channels per square centimeter.

9. The sequencing device according to claim 1, wherein:
   the memory includes further program instructions; and
   the processor is further configured to execute the program instructions to;
   rinse the first microfluidic gap to remove undesired cellular constituents of the only one cell from the cavity and/or the first microfluidic gap and to isolate the cellular DNA in the cavity; and
   fill the first microfluidic gap and the second microfluidic gap with a sequencing buffer.

10. The sequencing device according to claim 9, wherein the processor is further configured to execute the further program instructions to rinse the first microfluidic gap to remove undesired cellular constituents of the only one cell from the cavity and/or the first microfluidic gap by introducing a rinse liquid into the first microfluidic gap by a laminar flow.

11. The sequencing device according to claim 9, wherein the processor is further configured to execute the program instructions such that the rinsing of the first microfluidic gap diffuses the undesired cellular constituents of the only one cell from the cavity into the first microfluidic gap.

12. The sequencing device according to claim 1, wherein the processor is configured to execute the program instructions to feed the sample solution into the first microfluidic gap by feeding an aqueous solution containing cells into the first microfluidic gap.

13. The sequencing device according to claim 1, wherein the processor is configured to execute the program instructions to feed the sample solution into the first microfluidic gap by carrying out one or more of a centrifugation, a sedimentation, and a vacuum treatment to introduce the cell into the cavity.

14. The sequencing device according to claim 1, wherein the processor is configured to execute the program instructions to lyse the only one cell by carrying out at least one of the group consisting of a chemical lysis, an enzymatic lysis, an electrical lysis, an ultrasonic lysis, and a thermal lysis to release the cellular DNA.

15. The sequencing device according to claim 1, wherein the processor is configured to execute the program instructions to lyse the only one cell by introducing an organic phase into the first microfluidic gap by a laminar flow.

16. The sequencing device according to claim 1, wherein the processor is configured to execute the program instructions to sequence the cellular DNA in the pore by applying an electric voltage between a first substrate defining at least a portion of bounding the first microfluidic gap and a second substrate defining at least a portion of bounding the second microfluidic gap to sequence the cellular DNA in the pore.

17. The sequencing device according to claim 1, wherein:
the microfluidic sequencing channel opens directly to the first microfluidic gap with no constriction between the cavity and the second microfluidic gap;
    the microfluidic sequencing channel opens directly to the second microfluidic gap with no constriction between the pore and the second microfluidic gap; and
    the pore opens directly to the cavity with no constriction between the pore and the cavity.

18. The sequencing device according to claim 1, wherein the second microfluidic gap is defined by a continuous substrate opposite the pore.

* * * * *

UNITED STATES PATENT AND TRADEMARK OFFICE
CERTIFICATE OF CORRECTION

Page 1 of 2

PATENT NO. : 11,186,869 B2
APPLICATION NO. : 16/190308
DATED : November 30, 2021
INVENTOR(S) : Hoffmann et al.

It is certified that error appears in the above-identified patent and that said Letters Patent is hereby corrected as shown below:

In the Claims

In Claim 1, at Column 7, Line 49: "gapwith" should read --gap with--; and
   At Column 7, Line 54: "microfluidicgap" should read --microfluidic gap--.

In Claim 3, at Column 8, Line 14: "twomillimeters" should read --two millimeters--.

In Claim 4, at Column 8, Line 17: "thefirst" should read --the first--.

In Claim 6, at Column 8, Lines 22-23: "furthercomprising" should read --further comprising--.

In Claim 7, at Column 8, Line 26: "atleast" should read --at least--.

In Claim 8, at Column 8, Line 31: "squarecentimeter" should read --square centimeter--.

In Claim 9, at Column 8, Line 37: "onlyone" should read --only one--;
   At Column 8, Line 39: "inthe" should read --in the--; and
   At Column 8, Line 41: "asequencing" should read --a sequencing--.

In Claim 10, at Column 8, Line 43: "theprocessor" should read --the processor--.

In Claim 11, at Column 8, Line 53: "intothe" should read --into the--.

In Claim 12, at Column 8, Line 56: "firstmicrofluidic" should read --first microfluidic--.

In Claim 13, at Column 8, Line 61: "firstmicrofluidic" should read --first microfluidic--.

In Claim 14, at Column 8, Line 67: "outat" should read --out at--.

In Claim 15, at Column 9, Line 6: "introducingan" should read --introducing an--.

Signed and Sealed this
First Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,186,869 B2

In Claim 16, at Column 9, Line 10: "poreby" should read --pore by--.

In Claim 17, at Column 9, Line 20: "noconstriction" should read --no constriction--.

In Claim 18, at Column 9, Line 25: "thesecond" should read --the second--.